United States Patent [19]

Mango

[11] 4,297,294
[45] Oct. 27, 1981

[54] PROCESS FOR MAKING 4,4'-METHYLENE DIPHENYL DIISOCYANATE

[75] Inventor: Frank D. Mango, Houston, Tex.

[73] Assignee: Shell Oil Company, Houston, Tex.

[21] Appl. No.: 191,889

[22] Filed: Sep. 29, 1980

[51] Int. Cl.³ ............... C07C 118/02; C07C 119/048
[52] U.S. Cl. .................... 260/453 PH; 260/453 AM; 544/180; 564/331; 564/333
[58] Field of Search ............... 260/453 AM, 453 PH; 564/331, 333

[56] References Cited

U.S. PATENT DOCUMENTS

| | | | |
|---|---|---|---|
| 2,818,433 | 12/1957 | Erickson | 260/570 |
| 2,974,168 | 3/1961 | Sharp et al. | 260/570 |
| 3,476,806 | 11/1969 | Wolf | 260/570 |
| 3,676,497 | 7/1972 | Recchia et al. | 260/570 D |

FOREIGN PATENT DOCUMENTS

| | | |
|---|---|---|
| 803216 | 2/1974 | Belgium . |
| 815840 | 12/1974 | Belgium . |
| 109615 | 11/1974 | German Democratic Rep. . |
| 1365190 | 4/1972 | United Kingdom . |
| 1277740 | 6/1972 | United Kingdom . |
| 1341018 | 12/1973 | United Kingdom . |

Primary Examiner—Dolph H. Torrence
Attorney, Agent, or Firm—Dean F. Vance

[57] ABSTRACT

A novel process for making 4,4'-methylene diphenyl diisocyanate and corresponding oligomer in improved selectivity and yield comprises condensing formaldehyde and aniline under neutral or basic conditions to yield an anil condensate, followed by reacting the anil condensate with additional aniline and a protonic salt of aniline to yield 4,4'-methylene dianiline and corresponding oligomer, then followed by conventional phosgenation.

9 Claims, No Drawings

PROCESS FOR MAKING 4,4'-METHYLENE DIPHENYL DIISOCYANATE

BACKGROUND OF THE INVENTION

1. Field of the Invention

This invention is directed to a process for the production of 4,4'-methylene diphenyl diisocyanate and its associated oligomers in high yields and improved selectivity.

2. Description of the Prior Art

Organic isocyanates are materials of commerce employed in the production of polyurethane resins. Of increasing commercial importance are the polymethylene polyphenyl isocyanates, referred to as PMPPI. One member of the PMPPI family, 4,4'-methylene diphenyl diisocyanate, referred to in the industry as 4,4'-MDI, is especially desirable because it exhibits outstanding properties in polyurethanes.

The common process for preparing 4,4'-MDI and PMPPI is the phosgenation of the corresponding diamine (4,4'-MDA) and polyamine (PMPPA). The common process for preparing MDA and PMPPA is by the acid condensation of aniline and formaldehyde. Representative patents on this process and variations therein include U.S. Pat. No. 2,638,730, U.S. Pat. No. 2,818,433, U.S. Pat. No. 2,974,168, U.S. Pat. No. 3,476,806, U.S. Pat. No. 3,676,497, U. K. Pat. No. 1,277,740, U. K. Pat. No. 1,341,018, U. K. Pat. No. 1,365,190, Bel. Pat. No. 803,216, Bel. Pat. No. 815,840 and E. Germ. Pat. No. 109,615. In the presence of hydrochloric acid, formaldehyde condenses with aniline yielding a mixture of methylene bridged dimers (MDA), trimers (DMTA) and higher oligomers (PMPPA):

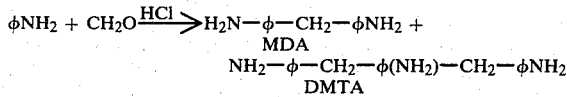

The mechanism is believed to involve the intermediacy of the imine $\phi N{=}CH_2$ which, on protonation, yields a key carbonium ion intermediate

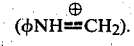

Aniline is then alkylated with high para-selectivity to another intermediate, I. This intermediate (I) can then undergo proton

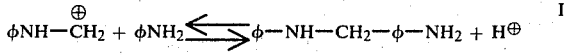

addition at nitrogen giving the amino benzyl cation II, which, in turn, completes the condensation by adding to a second molecule of aniline:

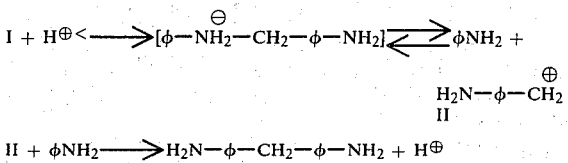

However, other processes can easily contribute, including a simple direct attack of the protonated formaldehyde (or some derivative), the direct counterpart to acetone-phenol condensation. The result is that the purity (selectivity) to the para-para isomer (4,4'-MDA) is not as high as desired. Further, the acidic conditions required in the typical condensation process present further problems. What is needed is a more selective, higher yielding process for the preparation of 4,4'-MDI and PMPPI.

SUMMARY OF THE INVENTION

The present invention broadly encompasses a novel and non-obvious process for the selective production of 4,4'-methylene diphenyl diisocyanate and corresponding oligomers, consisting essentially of the steps of:

(a) condensing formaldehyde with aniline under neutral or basic conditions to yield an anil condensate;

(b) reacting said anil condensate with aniline and a protonic salt of aniline under acidic conditions to yield an intermediate product selected from the group consisting of 4,4'-methylene dianiline, its corresponding oligomers and mixtures thereof; and (c) reacting said intermediate product with phosgene to yield the corresponding diisocyanate or polyisocyanate.

An important aspect of the present invention is the three step process wherein the formaldehyde and aniline are first condensed under *neutral* or *basic* conditions, as opposed to the *acidic* conditions employed in the prior art.

In the absence of acid, aniline and formaldehyde undergo an entirely different kind of condensation. Where the acid process results in exclusive *carbon* alkylation (ring coupling), acid-free condensation yields a complex mixture of products, all having one feature in common; they are exclusively *nitrogen* alkylated. Like their acid-catalyzed counterparts, aniline groups are linked together through methylenes. However, the methylenes are attached to nitrogen atoms, not carbons. Unlike MDA and PMPPA, these materials all possess only monosubstituted aromatic rings. They are believed to be interconvertible through the anil, and are very stable under most conditions.

The anil condensates range from distinct compounds such as the triphenyl hexahydrotriazine III and dianiline methane IV to polymers of the general structure V and, very likely, the oligomers VI.

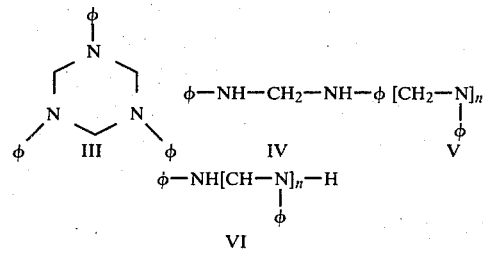

These materials have been prepared and the structural characteristics noted above have been verified, and have been found to be thermally unstable and difficult to characterize by the usual techniques such as TLC and GLC. TLC on silica, for example, yields only aniline and one faster eluting product; GLC gives a complex mixture of peaks suggesting substantial thermal decomposition.

There are three features of the anil condensates which make them excellent precursors to MDA. First each contains highly basic nitrogen atoms bonded to methylene units. Protonation should therefore yield species like

capable of ring attack and carbon alkylation. Second, each aromatic ring is attached to a nitrogen atom possessing at least one methylene unit. The reactivity of these rings to electrophilic attack should be enhanced over that of aniline. Moreover, the bulk of the N-attached carbon groups should enhance para-selectivity by sterically shielding the ortho positions. Finally, any conversion of the anil condensates to MDA condensates will entail the transformation of N—C bonds to C—C bonds and C—H bonds to N—H bonds, an overall energetically favorable process.

As shown in the Illustrative Embodiments which follow, the process according to the present invention results in greater selectivity to the para-para isomer and greater yield of desired product than does the two step, standard acid condensation-phosgenation process.

DETAILED DESCRIPTION OF THE INVENTION

In the first step aniline and formaldehyde are condensed under neutral or basic conditions (pH of 7.0 or greater) to form an anil condensate as defined above. Formaldehyde is conveniently used in the present process in the form of an aqueous solution such as formalin (a 37% aqueous solution). It is to be understood that formaldehyde generators such as paraform and trioxane which generate formaldehyde also may be used.

Selectivity to the various anil condensate components can be guided by changes in the aniline to formaldehyde ratio. Typical molar ratios of aniline to formaldehyde are between about 1:2 and about 3:1, preferably about 1:1. Reaction temperatures are typically between about 0° C. and about 80° C., preferably between about 40° C. and about 80° C., more preferably between about 55° C. and about 65° C. The reaction temperature does not appear to be critical to the reaction. Reaction time should be sufficient to ensure complete conversion of the formaldehyde.

The most critical aspect of the first step is that the reaction takes place under neutral (pH of 7.0) or basic (pH greater than 7.0) conditions. Since aqueous aniline solutions have a pH above 7.0, it is not necessary to add additional basic compounds. However, if desired the reaction may be undertaken in the presence of basic materials such as NaOH, NaHCO$_3$ and NH$_4$OH.

After the first step one may either recover the anil condensate or procede with the reaction to the amine in aqueous solution. Recovery of the anil condensate may be accomplished by standard solid-liquid separation procedures.

In the second step, the anil condensate is reacted with aniline in the presence of a protonic salt of aniline. The protonic salt of aniline acts as a catalyst in the reaction. The molar ratio of aniline to anil condensate (based on methylene (CH$_2$) equivalents present in the anil condensate) varies from about 1:1 to about 6:1, preferably about 2:1 to about 4:1. The molar ratio of protonic salt of aniline to added aniline varies from about 1:10 to about 1:2, preferably about 1:3 to about 1:5. Reaction temperatures in this step varies from about 60° C. to about 110° C., preferably about 80° C. to about 100° C.

The term "protonic salt of aniline" refers to an addition salt of an inorganic or organic acid with aniline which will dissociate in the process and release the free acid as a proton source. Illustrative of said inorganic and organic acid proton sources are inorganic acids such as hydrochloric acid, hydrobromic acid, hydriodic acid, hydrofluoric acid, sulfuric acid, phosphoric acid, silicic acid, fluosilicic acid, phosphomolybdic acid, and the like; and organic acids particularly hydrocarbon carboxylic acids from one to 12 carbon atoms, inclusive, such as alkanoic acids, for example, formic, acetic, butyric, caproic, caprylic, and lauric acids, alkane dicarboxylic acids, for example, oxalic, malonic, succinic, glutaric, adipic, and sebacic acids, alkenoic acids for example, acrylic, crotonic, and the like, aromatic carboxylic acids, for example, benzoic, toluic, phthalic, isophthalic, terephthalic, a-naphthoic, β-naphtholic, and the like, and araliphatic carboxylic acids such as phenylacetic, phenylpropionic, a-naphthaleneacetic acid, phenylvaleric acid, and the like. Preferred acids include HCl, HBr, HF and H$_2$SO$_4$, with HCl being most preferred.

After the reaction is completed, the reaction mixture in typically neutralized, water washed and the amine product is recovered. The amino product has a high proportion of the para-para isomer (typically greater than 85% weight para, para isomer). The amine product is then phosgenated under typical conditions to obtain the desired diisocyanates and polyisocyanates. See, for example, Kirk-Othmer, "Encyclopedia of Chemical Technology." Second Edition, Volume 12, pages 53 et seq, where the typical conditions for phosgenation are given.

The invention is further illustrated by reference to the following Illustrative Embodiments, which are given for the purpose of illustration only and are not meant to limit the invention to the particular reactants and conditions employed therein.

Illustrative Embodiment I

In Illustrative Embodiment I an anil condensate mixture was formed and analyzed. Aniline (120 mililiters (ml)) and 200 ml of H$_2$O were added to a 2 liter (l) flask with stirring. The ice-cooled mixture was treated with 112 gms of 37% formaline solution (1:1 mole ratio $\phi$NH$_2$:CH$_2$O) over 25 minutes. The white solid product was filtered, washed with one liter H$_2$O and dried in an oven under low vacuum (70° C.) overnight. The crude product (128 gm) had a broad melting range (mp=100°–230° C.).

About half of this product (∼64 gm) was extracted with boiling ethanol, filtered rapidly and allowed to cool. The crystals (2 gm, mp 134°–138° C. to clear liquid) were consistent with N,N,N-triphenylhydrotriazine. The white solid remaining after alcohol extraction (44 gm, melting 140°–248° C. to a white polymeric material) was analyzed by high resolution infra red technique (ir). The spectrum was definitely aromatic, free of paraformaldehyde absorption, and showed strong bands where monosubstituted aromatics absord (691 cm$^{-1}$, 755 cm$^{-1}$ and 743 cm$^{-1}$). There was no evidence of N—H or CH$_3$ bonds. The spectrum did contain obvious bands for CH$_2$ at 2925 cm$^{-1}$, 2850 cm$^{-1}$ and 1470 cm$^{-1}$, consistent with

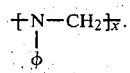

The ir spectrum of the crude product (mp 100°–230° C.) contained bands in the N—H region indicating the structure

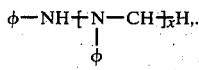

Illustrative Embodiment II

This run was typical of a number of anhydrous runs carried out using different anil condensates and reaction conditions. In this reaction the condensate isolated above in Illustrative Embodiment I

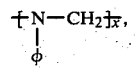

mp 140°–248° C.) was used.

These were runs seeking qualitative information on the reactivities of the respective condensates. In this run (1.5 hr, 90° C.), conversion of condensate to PMPPA was approximately 90%.

The ratio $\phi NH_2/CH_2$ was 3 and $HCl/\phi NH_2$ was 0.27. The reactants were therefore used in the following molar amounts:

$$\frac{(0.10 \text{ moles } \phi NCH_2) + }{(0.12 \text{ moles } \phi NH_2) + (0.08 \text{ moles } \phi NH_3Cl)}$$
$$\frac{(0.10 \text{ moles } \phi NCH_2)}{(0.8 \text{ moles } \phi NH_3Cl)}$$
$$\frac{(0.10 \text{ moles } \phi NCH_2) +}{(0.12 \text{ moles } \phi NH_2) + (0.08 \text{ moles } \phi NH_2Cl)}$$

The above reactants were added to a 50 ml Bantam resin kettle, top-fitted with a mechanical stirrer. The hydrochloride was added last at room temperature, and the mixture stirred for 1 hour. The temperature of the mixture rose slightly (28° C. to 31° C.) during this period. The reaction mixture was then placed in a 90° C. oil bath and stirred. A clear, yellow solution resulted. After about 10 minutes, a yellow, salt-like precipitate formed and remained in the system for the remainder of the reaction (total time at 90° C., 1.5 hours).

The product was made basic with NaOH solution (10%), and washed with water. The water fractions were extracted with ether, and the entire organic product dried and the ether removed under reduced pressure. The MDA of the crude product was approximately 90% 4,4'-MDA.

In another reaction similar to the above, the salt-like precipitate formed in the initial part of the run, was completely dissolved into a clear solution by the addition of 5 ml $H_2O$.

Reactions in aniline solution using the individual anil condensates (III, IV, and V) were carried out as well as reactions with mixtures of unknown composition. The reaction conditions were varied from 80° C. to 90° C. with the ratios of aniline equivalents/$CH_2$ varying from 6 to 3 and HCl/aniline equivalents around 0.3. In all cases, anil condensates are converted to MDA and PMPPA. The reactions appeared clean with respect to conversion of anil condensate. The products gave clean GLC spectra, a characteristic not shared by the anils themselves. Because these first reactions were generally water-free, problems were encountered from salt-like solid precipitates forming in the reactor early in the reaction period. This generally occurred at low aniline equivalents/$CH_2$ ratios and the higher concentrations of HCl. The salting effect very likely limits conversion and may have an adverse effect on selectivity.

The GLC trace of a typical product was identical to that of a commercial mixture of MDA and PMPPA. A vacuum distilled cut of the MDA product proved to be primarily 4,4'-MDA, the identification made from $^1H$, $^{13}C$ nmr, GLC-MS and comparisons with the genuine compound. $^{13}C$ nmr proved an effective tool in assessing the degree of conversion to pure MDA. At incomplete conversion, the $CH_2$ region showed the single band associated with the known intermediate $\phi$-NH-$CH_2$-$\phi$-$NH_2$. At higher conversions (longer reaction periods), this peak diminishes and the one associated with MDA ($H_2N\phi$-$CH_2$-$\phi$-$NH_2$) increases. Crude product spectra were very clean, essentially free of peaks not in that of the commercial product.

Selectivities (basis GLC) to 4,4'-MDA varied from 82 to 90% of the MDA product. Complete material balances and conversions are difficult to determine in batch reactions where the products are mixtures of high molecular weight compounds. In one reaction, using an internal standard and predetermined GLC % w factors, a reasonable overall material balance (98%) was obtained. Polymeric anil V (mp 140°–148° C.), an aniline equivalent/$CH_2$ ratio of 4.2, HCl/aniline equivalents of 0.2 and a reaction period of one hour at 80° C. and two hours at 90° C. gave a conversion of anil condensate to product of 75%. The remaining anil is converted to aniline, presumably during workup. The limited conversion could be a consequence of the salt precipitate noted earlier. The reaction proceeded with 85% selectivity to the 4,4' isomer in the MDA mixture and 90% MDA in the total product.

Illustrative Embodiment III

In this series of reactions, water was added to the anil condensate runs to equal that in their respective duplicate formaldehyde runs (approximately 20% w). As noted above, the addition of water to anhydrous reacting solutions of anil condensate eliminates any problems associated with the precipitations; these reactions were invariably homogeneous liquid systems.

A series of reactions were carried out in twin glass reactors. They were maintained at 90° C. for 4 hours under constant stirring. In all experiments, the ratio of HCl to $\phi NH_2$ was kept at 0.3 while $\phi NH_2/CH_2$ was varied from 2 to 4. In the runs summarized in Table I, the anil used was the preformed solid material (mp 100°–230° C.) of the general structure from Illustrative Embodiment I $\phi$-NH(N$\phi$CH$_2$)$_x$H. The anil condensate used in these runs was a crude product composed of a blend of oligomers containing an unknown amount of aniline equivalents as evidenced by N—H absorption in the ir. Because the methylene content of the anil was uncertain, but lower than theoretical (theoretical being $+N\phi$-$CH_2+$), aniline conversion would be expected to be lower than that of the complete condensate $+N\phi$-$CH_2+$. This is the case in Table I, which shows a lower conversion of aniline from the anil than from its comparative formaline runs. The lower aniline conversion is, of course, not real, but only a numerical artifact resulting from the method used to calculate conversion (which did not account for the excess aniline equivalents in the starting condensate). The comparative selectivity results are, however, real as are those on yield, basis starting material. The yield results in the anil runs are of significance in that the starting anil actually contained less CH₂ equivalents than the formaline runs, yet yielded as much MDA+DMTA and slightly more MDA. Included in Table I is a run using anil condensate formed in situ where no ambiguities exist regarding the amounts of aniline and methylene equivalents used in the reactions. Under the conditions indicated, the anil condensate gives a higher yield of lighter oligomers (MDA) and a higher selectivity to the more desirable 4,4'-isomer.

The results presented in Table I under the heading "Acid Condensation-37% Formation", are employed as a comparison against the prior art process. The reaction described here for $\phi NH_2/CH_2 = 2$ and $HCl/\phi NH_2 = 0.3$ is typical of those carried out to match the anil runs. A mixture of aniline (6.51 gm, distilled from Zn), aniline hydrochloride (3.88 gm) and 2.5 ml 0.1 N NaOH was added to the glass stirred reactor and the 37% formaline solution (4.05 gm) added followed by 2.5 ml 0.1 N HCl added with stirring at 90° C. After 4 hours this reaction product was cooled, and worked up exactly as were their comparative anil reactions.

TABLE I

COMPARATIVE YIELD DATA
FOR ANIL CONDENSATE (N$\phi$CH₂)
AND CONVENTIONAL ANILINE-
FORMALDEHYDE CONDENSATION 90° C., 4 Hr $\frac{NH_2}{CH_2} = 3.0; \frac{HCl}{\phi NH_2} = 0.3$

|  | Acid Condensation 37% Formalin* | Preformed Anil* | Anil Formed In Situ |
|---|---|---|---|
| Aniline Conversion, % w | 59 | 53 | 59 |
| Selectivity |  |  |  |
| 4,4' MDA in MDA | 85 | 90 | 88 |
| MDA in crude product | 84 | 87 | 86 |
| Yield, % w |  |  |  |
| Basis Starting Material |  |  |  |
| MDA + DMTA | 53 | 53 | 56 |
| MDA | 45 | 46 | 48 |
| Basis Converted Aniline |  |  |  |
| MDA + DMTA | 95 | 105 | 99 |
| MDA | 80 | 90 | 85 |

TABLE I-continued

COMPARATIVE YIELD DATA
FOR ANIL CONDENSATE (N$\phi$CH₂)
AND CONVENTIONAL ANILINE-
FORMALDEHYDE CONDENSATION 90° C., 4 Hr $\frac{NH_2}{CH_2} = 3.0; \frac{HCl}{\phi NH_2} = 0.3$

|  | Acid Condensation 37% Formalin* | Preformed Anil* | Anil Formed In Situ |
|---|---|---|---|
| 4,4' MDA | 67 | 81 | 74 |

*Data the Average of Three Runs

Illustrative Embodiment IV

In these reactions, the anil condensates were preformed in the reactor by rapidly stirring a 1:1 molar ratio of aniline-formaldehyde under mildly basic conditions. Stirring at 60° C. for about one hour produced a thick cream-like, white anil condensate. The appropriate amount of H₂O, aniline and aniline hydrochloride were then added to tightly match the comparative formaline run, and the reaction started with stirring at 90° C. for 4 hours.

Table II contains the results for the in situ anil runs and their respective formaline counterparts. Although only a limited number of experiments were carried out, the trends noted above persisted as the $\phi NH_2$-to-CH₂ molar ratio went from 2 to 4. Aniline conversions were remarkably consistent. The higher conversion noted for the anil condensate at $\phi NH_2/CH_2O = 2$ is probably real, reflecting the greater consumption of aniline that attends a product mix richer in lower oligomers.

Selected crude samples were thoroughly analyzed by $^{13}C$ nmr. These were entire products and not just fractions. The spectra were unusually clean, free of starting anil condensate adsorption as evidenced by the absence of N-bonded CH₂ or other bands not consistent with the expected MDA, PMPPA product mix.

Carbon assignments were made for ortho, meta and para substituted anilines. The total para content for the anil and formaline products at $\phi NH_2/CH_2 = 2$ was essentially the same, 56% mole for the two products. For both the 3 and 4 $\phi NH_2/CH_2$ ratio products, however, the anil reactions yielded a higher overall para product: 70 to 71 (anil) vs 59 to 60 (formaline) and 70 (anil) vs 66 (formaline), respectively.

TABLE II

COMPARATIVE YIELD DATA FOR ANIL CONDENSATE (PERFORMED, IN SITU)
WITH CONVENTIONAL ANILINE-FORMALDEHYDE CONDENSATION

| $\frac{\phi NH_2}{CH_2}$ | 2 | | 3 | | 4 | |
|---|---|---|---|---|---|---|
|  | Acid Condensation | Anil Condensate | Acid Condensation | Anil Condensate | Acid Condensation | Anil Condensate |
| Aniline Conversion, % w | 80 | 83 | 59 | 59 | 47 | 47 |
| Selectivity |  |  |  |  |  |  |
| 4,4' MDA in MDA | 89 | 94 | 85 | 88 | 84 | 90 |
| MDA in Crude Product | 78 | 80 | 84 | 86 | 86 | 89 |
| Yield, % w |  |  |  |  |  |  |
| Basis Starting Material |  |  |  |  |  |  |
| MDA + DMTA | 69 | 67 | 53 | 56 | 47 | 49 |
| MDA | 53 | 53 | 45 | 48 | 40 | 43 |
| 4,4' MDA | 48 | 50 | 38 | 42 | 34 | 39 |
| Basis Aniline Converted |  |  |  |  |  |  |
| MDA + DMTA | 92 | 85 | 95 | 99 | 102 | 107 |
| MDA | 71 | 68 | 80 | 85 | 88 | 96 |
| 4,4' MDA | 63 | 64 | 67 | 74 | 74 | 87 |

What is claimed is:

1. A process for the selective production of 4,4'-methylene diphenyl diisocyanate and corresponding oligomers, consisting essentially of the steps of:
   (a) condensing formaldehyde with aniline under neutral or basic conditions to yield an anil condensate;
   (b) reacting said anil condensate with aniline and a protonic salt of aniline under acidic conditions to yield an intermediate product selected from the group consisting of 4,4'-methylene dianiline, its corresponding oligomers and mixtures thereof; and
   (c) reacting said intermediate product with phosgene to yield the corresponding diisocyanate or polyisocyanate.

2. The process of claim 1 where said anil condensate is selected from the group consisting of

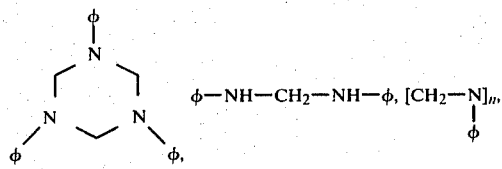

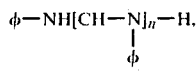

and mixtures thereof where n varies from 1 to about 200.

3. The process of claim 1 wherein step a takes place under basic conditions.

4. The process of claim 1 where said protonic salt of aniline is the addition salt of aniline with an acid selected from the group consisting of hydrochloric acid, hydrobromic acid, hydrofluoric acid and sulfuric acid.

5. The process of claim 4 wherein said protonic salt of aniline is aniline hydrochloride.

6. The process of claim 1 wherein the molar ratio of aniline to formaldehyde in step a is between about 1:2 and about 3:1.

7. The process of claim 1 or 6 wherein the molar ratio of aniline to anil condensate in step b is between about 1:1 and 6:1.

8. The process of claim 7 wherein molar ratio of said protonic salt of aniline to said aniline in step b is between about 1:10 and about 1:2.

9. The process of claim 1 wherein said anil condensate is recovered from step a prior to contact with aniline in step b.

* * * * *